(12) United States Patent
Aslan

(10) Patent No.: US 10,894,084 B2
(45) Date of Patent: Jan. 19, 2021

(54) METAL-ASSISTED AND MICROWAVE-ACCELERATED DECRYSTALLIZATION

(71) Applicant: Morgan State University, Baltimore, MD (US)

(72) Inventor: Kadir Aslan, Baltimore, MD (US)

(73) Assignee: Morgan State University, Baltimore, MD (US)

( * ) Notice: Subject to any disclaimer, the term of this patent is extended or adjusted under 35 U.S.C. 154(b) by 605 days.

(21) Appl. No.: 15/356,984

(22) Filed: Nov. 21, 2016

(65) Prior Publication Data

US 2017/0143829 A1 May 25, 2017

Related U.S. Application Data

(60) Provisional application No. 62/386,153, filed on Nov. 19, 2015.

(51) Int. Cl.
*A61K 41/00* (2020.01)
*A61N 5/02* (2006.01)
(Continued)

(52) U.S. Cl.
CPC ...... *A61K 41/0028* (2013.01); *A61B 18/1815* (2013.01); *A61K 9/08* (2013.01);
(Continued)

(58) Field of Classification Search
CPC combination set(s) only.
See application file for complete search history.

(56) References Cited

U.S. PATENT DOCUMENTS

| | | | | |
|---|---|---|---|---|
| 2006/0190063 A1* | 8/2006 | Kanzius | ............... | A61N 1/406 607/101 |
| 2012/0190912 A1* | 7/2012 | McKenna | ............ | A61B 5/0059 600/12 |
| 2015/0032046 A1* | 1/2015 | Deborski | ................ | A61N 7/00 604/21 |

OTHER PUBLICATIONS

Aslan et al. De-crystallization of Uric Acid Crystals in Synovial Fluid Using Gold Colloids and Microwave Heating. Nano Biomed. Eng. 2014, 6(4), 104-110 (hereinafter, "Aslan") (Year: 2014).*

* cited by examiner

*Primary Examiner* — Joseph A Stoklosa
*Assistant Examiner* — Adam J Avigan
(74) *Attorney, Agent, or Firm* — Whiteford, Taylor & Preston, LLP; Peter J. Davis

(57) ABSTRACT

In this study, we demonstrated a unique application of our Metal-Assisted and Microwave-Accelerated Decrystallization (MAMAD) technique for the de-crystallization of uric acid crystals, which causes gout in humans when monosodium urate crystals accumulate in the synovial fluid found in the joints of bones. Given the shortcomings of the existing treatments for gout, we investigated whether the MAMAD technique can offer an alternative solution to the treatment of gout. Our technique is based on the use of metal nanoparticles (i.e., gold colloids) with low microwave heating to accelerate the de-crystallization process. In this regard, we employed a two-step process; (i) crystallization of uric acid on glass slides, which act as a solid platform to mimic a bone, (ii) de-crystallization of uric acid crystals on glass slides with the addition of gold colloids and low power microwave heating, which act as "nano-bullets" when microwave heated in a solution. We observed that the size and number of the uric acid crystals were reduced by >60% within 10 minutes of low power microwave heating. In addition, the use of gold colloids without microwave heating (Continued)

(i.e. control experiment) did not result in the de-crystallization of the uric acid crystals, which proves the utility of our MAMAD technique in the de-crystallization of uric acid.

5 Claims, 8 Drawing Sheets

(51) Int. Cl.
*A61B 18/18* (2006.01)
*A61K 9/16* (2006.01)
*A61K 9/08* (2006.01)
*A61K 33/24* (2019.01)
*A61N 1/40* (2006.01)

(52) U.S. Cl.
CPC ................ *A61K 9/16* (2013.01); *A61K 33/24* (2013.01); *A61N 1/406* (2013.01); *A61N 5/022* (2013.01); *A61N 5/025* (2013.01)

METAL-ASSISTED AND MICROWAVE-ACCELERATED DECRYSTALLIZATION

BACKGROUND OF THE INVENTION

Field of the Invention

The present invention relates to de-crystallization of uric acid crystals.

Description of the Background

Gout disease, or gouty arthritis, a disease that affects more than 8.3 million people in the U.S., arises from the deposition of monosodium urate (uric acid) crystals in joints, tendons, and bursae. Sustained elevations of the serum urate concentration (i.e. hyperuricemia) above the theoretic solubility limit of monosodium urate (6.8 mg/dL in a physiologic salt solution) are a prerequisite for the development of gout. The crystallization of uric acid in body tissues can occur when (i) the body increases the amount of uric acid it produces, (ii) the kidneys fail to excrete enough uric acid, (iii) dietary habits include consumption of food with high purine content and/or excessive alcoholic beverages, (iv) following organ transplantation, (v) a patient is overweight, or (vi) a patient has a weak metabolism or is otherwise unable to break down purines. The arthritis of gout is typically episodic in its early stages, triggered by the release of monosodium urate crystals from pre-formed deposits in the joints and periarticular tissues. As the disease progresses macroscopic deposits of monosodium urate (tophi) form leading to a chronic erosive arthritis. Gout is known to affect, inter alia, the hallux rigidus of the big toe with the symptoms of redness, stiffness and swelling of the big toe. In addition, other parts of the body (ankles, heels, knees, wrists, fingers, and elbows) can also be affected. Current therapies for gout include anti-inflammatory (NSAIDs and glucocorticoids) and urate-lowering drugs; the former are limited by treatment side-effects, including gastrointestinal ulceration and bleeding, renal dysfunction, osteoporosis, and increased infection risk while the latter are limited by the need for life-long adherence, potential for renal injury and rare life-threatening allergic reactions.

Accordingly, there is still an urgent need for new methodologies for the treatment of gout while minimizing the risks of other bodily complications.

SUMMARY OF THE INVENTION

The present invention uses Metal-Assisted and Microwave-Accelerated De-crystallization (MAMAD) technology in which sterile metal colloids, preferably gold colloids, are excited by microwave energy for the removal of gout-inducing uric acid crystals deposited in human tissues and joints. The absorption/reflection of electromagnetic energy and subsequent conversion to additional kinetic energy by metal nanoparticles exposed to microwave irradiation is a highly innovate and unique approach for the treatment of gout. This innovative method of treatment may improve the overall quality of life for millions of Americans suffering from the chronic pain caused by gout and its associated comorbidities and reduce the need for pharmaceutical drugs.

The utility of the MAMAD technology for treatment of gout was demonstrated by the use of metal colloids in solution and immobilization of uric acid crystals on a solid surface (FIG. 1), where a microwave-induced temperature gradient exists. Metal colloids in solution convert the microwave energy to kinetic energy to move about the uric acid solution for the de-crystallization process, where the collisions between the metal colloids and uric acid result in the break down uric acid crystals.

In the experiments described herein, the inventors demonstrated the de-crystallization of uric acid crystals in the presence of gold colloids and low power microwave heating. Colloidal gold is a sol or colloidal suspension of submicrometer-size nanoparticles of gold in a fluid, usually water.

In order to simulate the conditions in the human body, first, uric acid crystals were grown on glass slides (a model bone surface). Subsequently, gold colloids in synovial fluid was added to the glass slides with uric acid crystals and were exposed to microwave heating or incubated at room temperature. The exposure of uric acid crystals to microwave heating in the presence of gold colloids resulted in up to 60% reduction in the number of uric acid crystals. On the other hand, the use of colloids at room temperature (without microwave heating) or the use of microwave heating (without gold colloids) did not affect the number and size of the uric acids crystals, demonstrating the utility of using gold colloids and microwave heating together for the de-crystallization of uric acid crystals.

The gold colloids can be used in aggregated or completely dispersed form and do not need chemical additives to prevent aggregation. Metal colloids with different sizes (20-200 nm diameter) and concentrations (1× and 100×) are generally suitable. Different sizes of the metal colloids can be useful in the potential treatment of gout at different stages, and area of application (e.g, tissue, joint).

Any metal colloid can be used according to the invention. Preferred metal colloids are silver, gold, copper, aluminum, zinc, chromium, palladium, nickel, rhodium, iron, platinum, tin, gallium, indium, cadmium, cobalt, manganese, and ruthenium colloids.

In one embodiment of the present invention, these metal colloids can be used alone. In others embodiment of the present invention, two or more of these metal colloids can be used at the same time.

Any suitable particle size can be used for the metal colloids from 2 nanometers to 2000 nanometers, but preferably 20 nm to 200 nm in diameter.

Any suitable microwave frequency can be used. A preferred microwave frequency ranges from 0.3 to 30 GHz. A particularly preferred microwave frequency is 2.45 GHz. Any suitable microwave power can be used. A preferred microwave power range is 1 W-30000 W. A particularly preferred microwave range is 1 W-1200 W.

BRIEF DESCRIPTION OF THE DRAWINGS

The numerous advantages of the present invention may be better understood by those skilled in the art by reference to the accompanying drawings in which.

DETAILED DESCRIPTION

Figure 1:
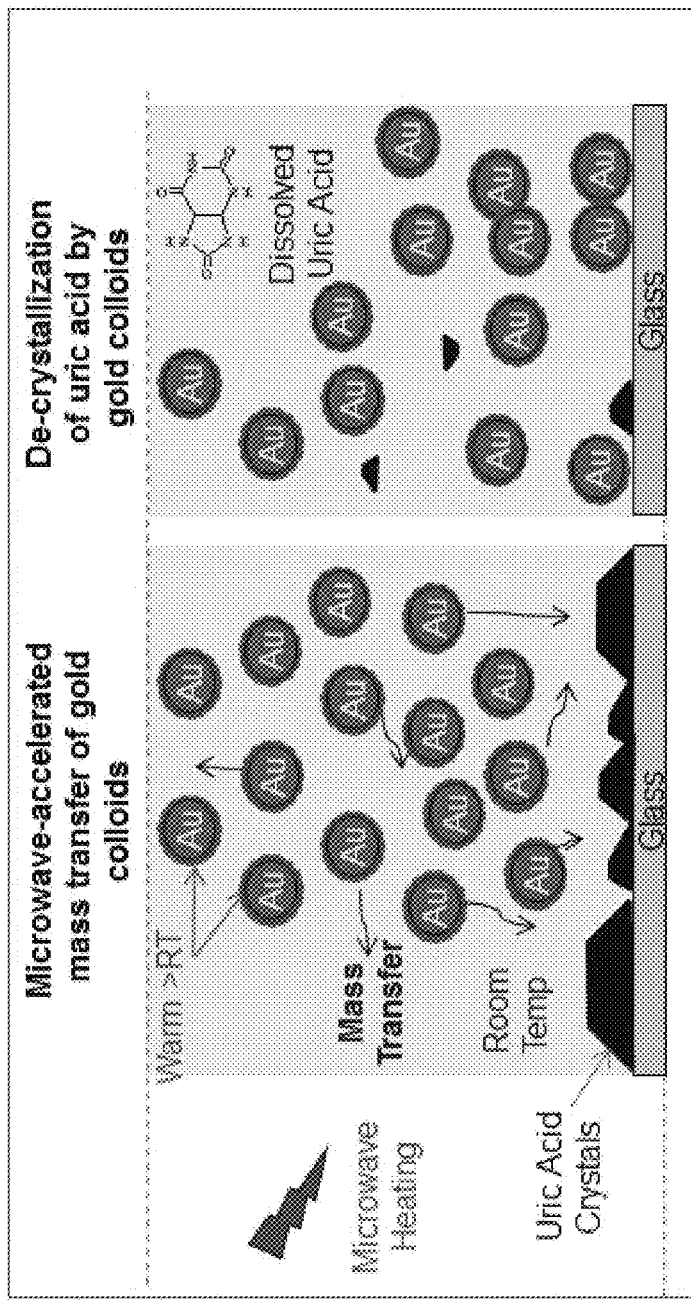
FIG. 1 is a depiction of the de-crystallization of uric acid crystals using gold colloids with microwave heating.

The following description is of a particular embodiment of the invention, set out to enable one to practice an implementation of the invention, and is not intended to limit the preferred embodiment, but to serve as a particular example thereof. Those skilled in the art will appreciate that they may readily use the conception and specific embodiments disclosed as a basis for modifying or designing other methods and systems for carrying out the same purposes of the present invention. Those skilled in the art will also realize that such equivalent assemblies do not depart from the spirit and scope of the invention in its broadest form.

In MAMAD, upon exposure to microwave heating, a thermal gradient is created between the solution and the metal nanoparticles due to a ~620-fold difference in the thermal conductivity of metal (silver −429 W/mK) and water (0.61 W/mK). This thermal gradient results in the transfer of metal nanoparticles from the warmer solution to the cooler nanoparticles in an effort to thermally equilibrate the system. Subsequently, the following sequence of events occurs: 1) microwave heating increases the velocity of the metal nanoparticles, 2) the higher velocity metal nanoparticles collide with the target crystal structures frequently and 3) these collisions result in the breakdown of the target crystal structures. Since the number of metal colloids ($1 \times 10^{11}$ particles/mL) is significantly larger than the number of uric acid crystals (which are 1000-fold larger in size than metal colloids of ~50 nm in diameter), these collisions result in the fracturing and eventual reduction in size of the uric acid crystals. In addition, a controllable increase in the temperature of the medium (up to 10° C.) with microwave treatment can also result in partial dissolution of the uric acid crystals.

EXAMPLE 1

Materials

Sulfuric acid and hydrogen peroxide purchased from Pharmco products Inc. Deionized water purified via a Millipore Direct Q 3 UV apparatus. Glass slides of 0.96 to 1.06 mm thickness purchased from Corning Incorporated. Uric acid and 20 nm gold colloids purchased from Sigma-Aldrich (USA, catalog number: 741965: ~$7.2 \times 10^{11}$ particles/mL). Silicon isolators composed of 12 wells (30 µL capacity) and targets (57 mm in diameter) purchased from Electron Microscopy Sciences.

Methods

The standard glass microscope slides were cut into eight equal pieces, cleaned and submerged in freshly prepared piranha solution (3:1 Sulfuric Acid: Hydrogen Peroxide) for 10 minutes, followed by thorough rinse with deionized water and air dry process. Silicon isolators (2.0 mm deep and 4.5 mm diameter) were attached to one piece of the cut glass slides. 20 µL uric acid solution (prepared by mixing 10 mg of uric acid with 20 mL of deionized water) was added to each wells and allowed to crystallize at room temperature.

Figure 2:
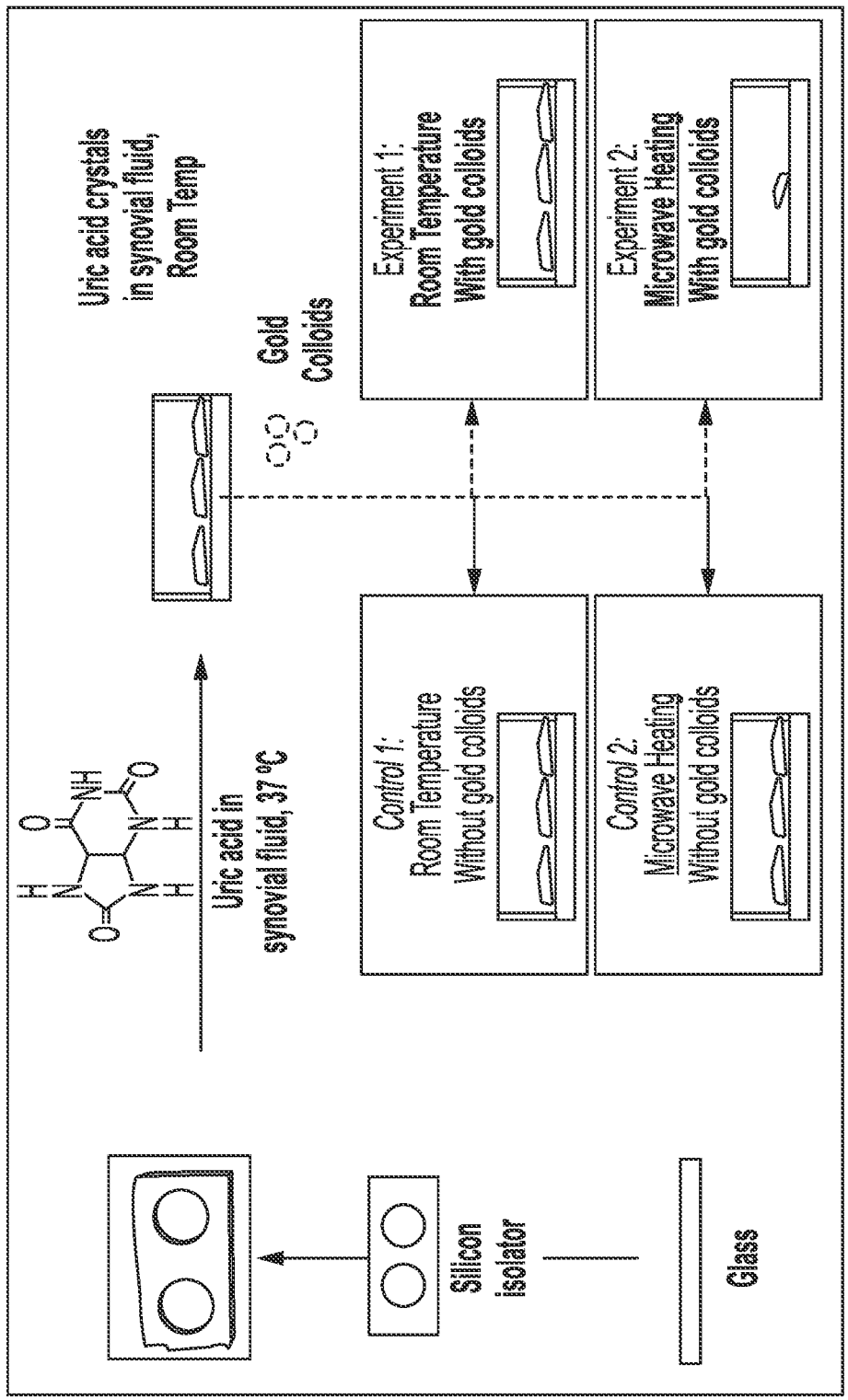
FIG. 2 is a representation of the experiments conducted which led to the present invention.
Figure 3A:
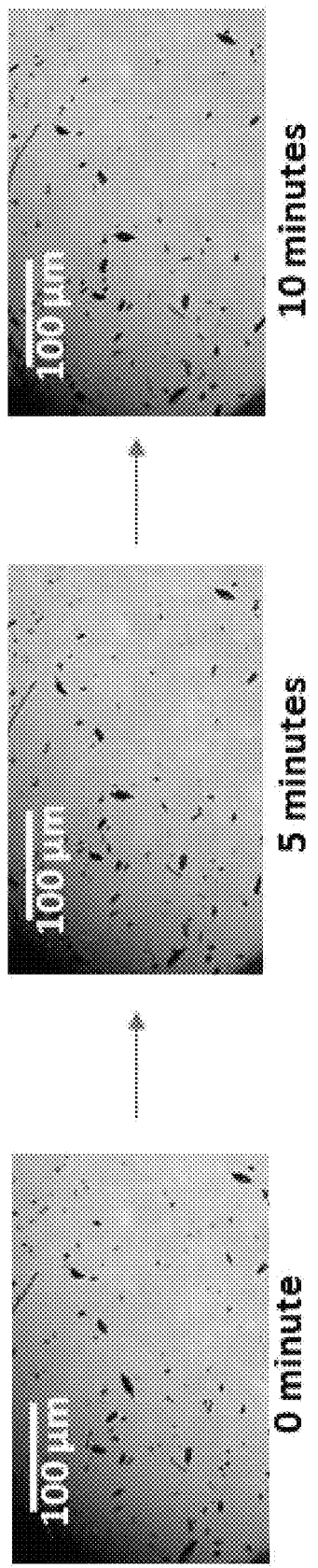
FIGS. 3A-3D show optical images of uric acid crystals grown on glass slides with and without gold colloids at both room temperature and microwave heating after 10 minutes of incubation for Experiment 1: Uric Acid Crystals with Gold Colloids at Room Temperature (FIG. 3A), Experiment 2: Uric Acid Crystals with Gold Colloids using Microwave_PL1 (FIG. 3B), Experiment 3: Control 1: Uric Acid Crystals without Gold Colloids at Room Temperature (FIG. 3C), and Control 2: Uric Acid Crystals without Gold Colloids using Microwave_PL1 (FIG. 3D).
Figure 3B:
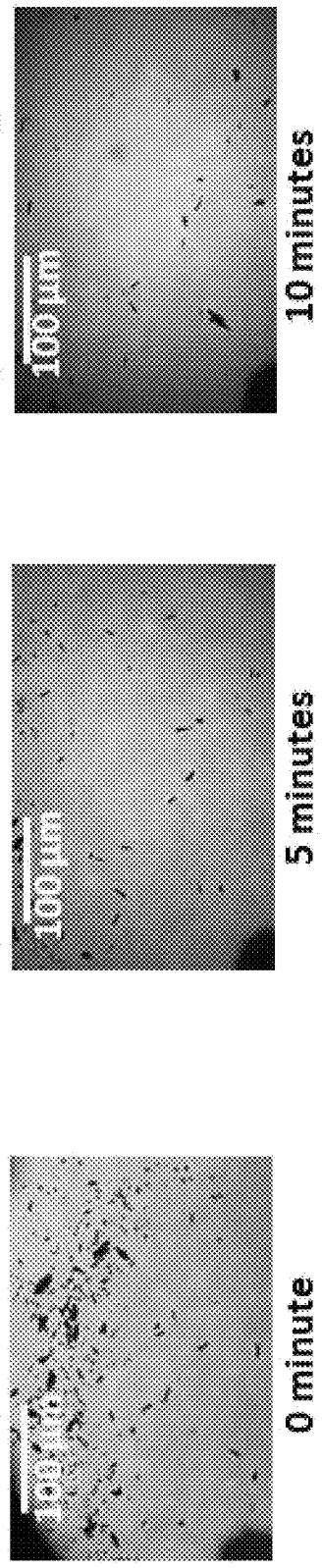
Figure 3C:
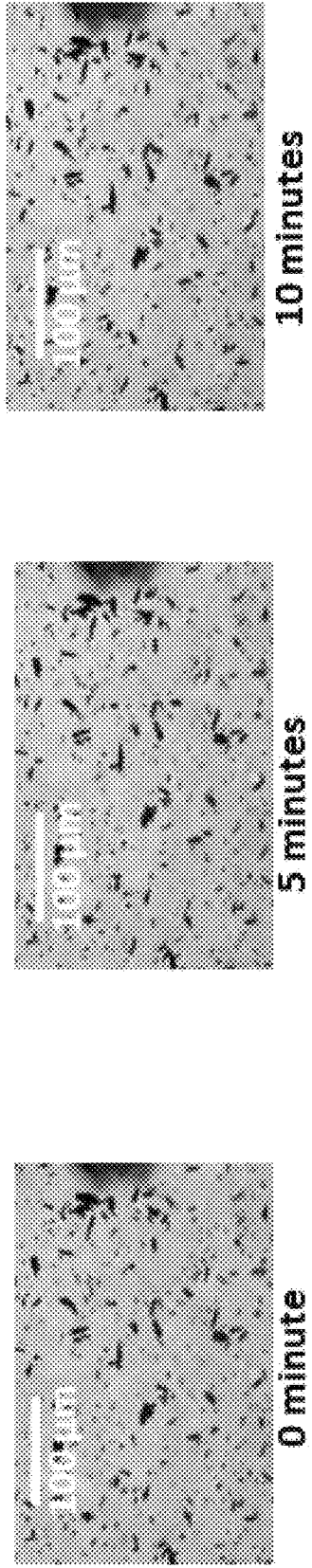
Figure 3D:
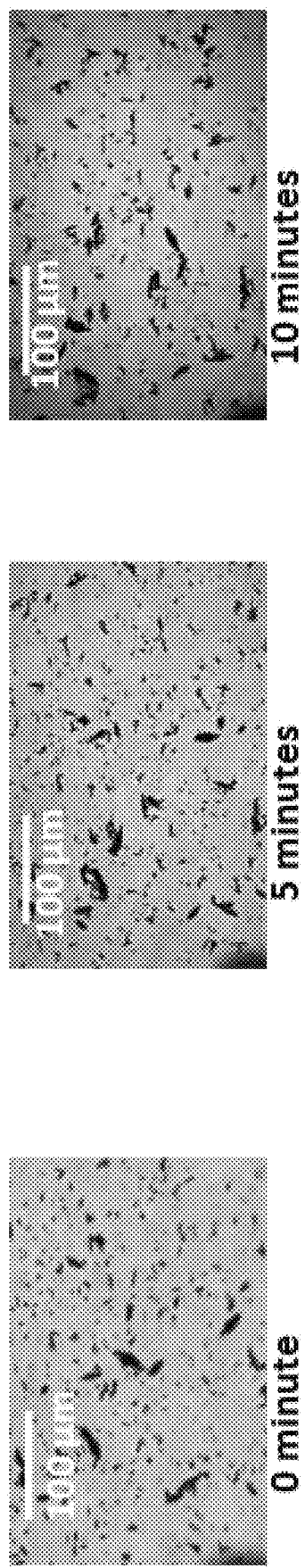

After uric acid crystals were grown, 10 µL of bovine synovial fluid at room temperature (from Lampire Biological Laboratories) was added to the wells and four different experiments were carried out (See FIG. 2):

a. Experiment 1: uric acid crystals with gold colloids at room temperature, where 10 µL of gold colloids was incubated inside the wells at room temperature;
b. Experiment 2: uric acid crystals with gold colloids using microwave heating, where 10 µL of gold colloids was incubated inside the wells using microwave heating (700 W output kitchen microwave, power level 1);
c. Control 1: uric acid crystals without gold colloids at room temperature, where 10 µL of deionized water without gold colloids was incubated inside the wells at room temperature;
d. Control 2: uric acid crystals without gold colloids using microwave heating, 10 µL of deionized water without gold colloids was incubated inside the wells using microwave heating.

Optical images of the crystals were taken at one minute increments with an optical microscope to observe de-crystallization uric acid crystals (i.e., the samples are taken out of the microwave for 30 sec). The number and size of uric acid crystals were monitored using Motic software.

Figures 4A, 4B:
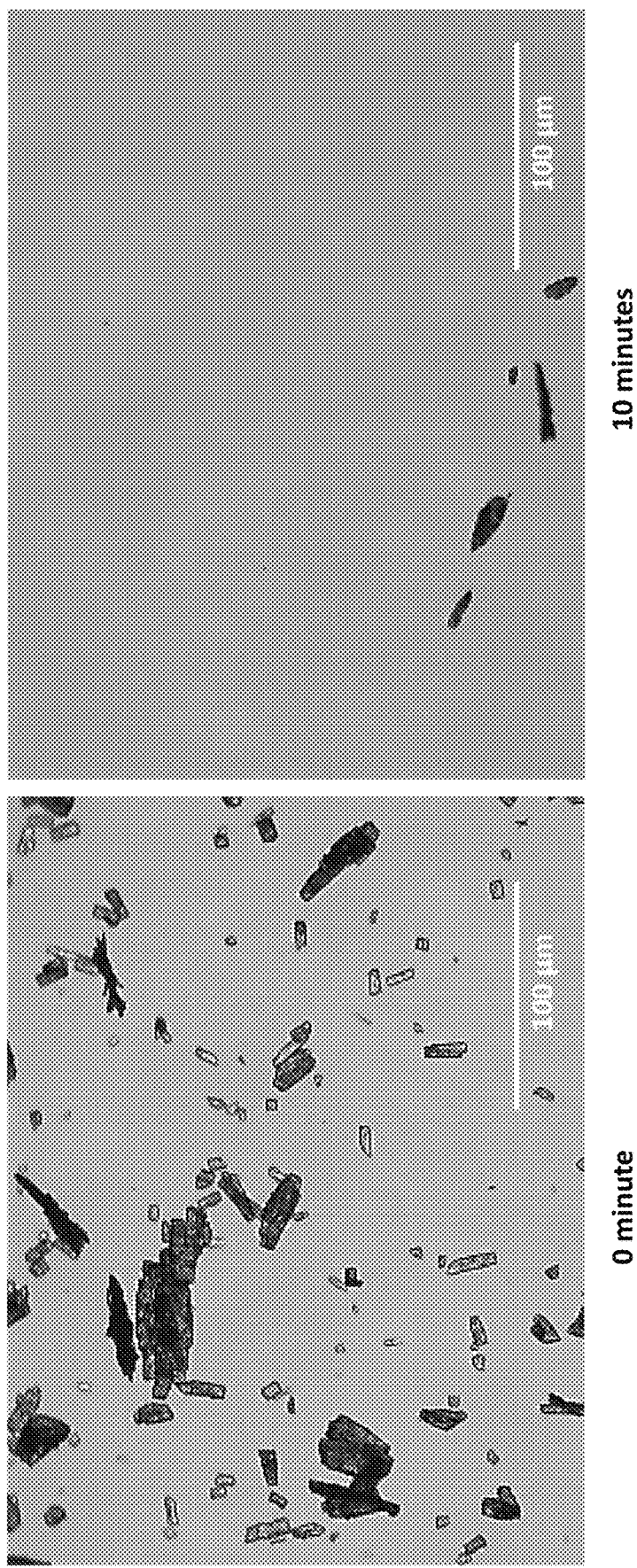
FIGS. 4A and 4B show high-resolution optical images of uric acid crystals grown on glass slides with gold colloids and using microwave heating before (FIG. 4A) and after 10 minutes of incubation (FIG. 4B), Experiment 2, Uric Acid Crystals with Gold Colloids using Microwave_PL1.

FIG. 3 shows the comparison of optical images of uric acid crystals with and without gold colloids incubated at room temperature and using microwave heating. In Experiment 1 and Control 1, the size and the number of uric acid crystals remained the same after 10 minutes of incubation. The same observation was also made when a solution without gold colloids was incubated with uric acid crystals with microwave heating (Control 2). On the other hand, the use of gold colloids with microwave heating (Experiment 2) resulted in a significant reduction in the number and size of uric acid crystals after 10 minutes. FIG. 4 shows the higher resolution optical images of uric acid crystals in Experiment 2 which reveal that the initial size of the uric acid crystals (t=0 min) was 25±16 µm. The smaller uric acid crystals also appeared to be in an isolated form and aggregated form. However, after the addition of gold colloids and exposure to microwave heating, the number and size of the uric acid crystals were significantly reduced.

Figure 5:
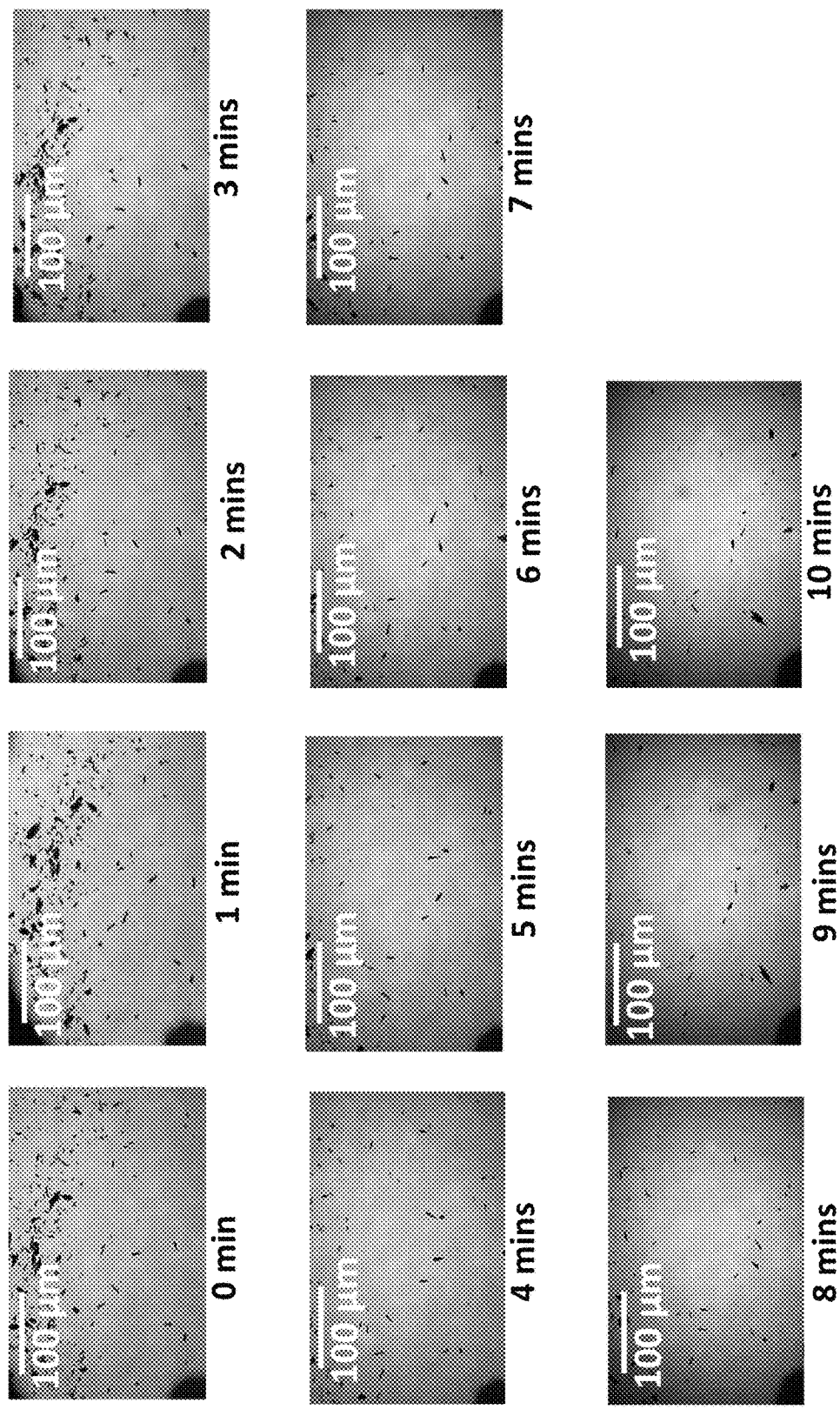
FIG. 5 shows a time progression of the de-crystallization of uric acid crystals on blank glass slides with gold colloids using microwave heating at power level 1.

FIG. 5 shows the time progression of uric acid crystals with the addition of gold colloids and microwave heating for 10 minutes. FIG. 5 also shows that the number of uric acid crystals was significantly reduced after 4 minutes of microwave heating. The average number of uric acid crystals in the beginning of each experiment used in this study was 70±10.

Figure 6:
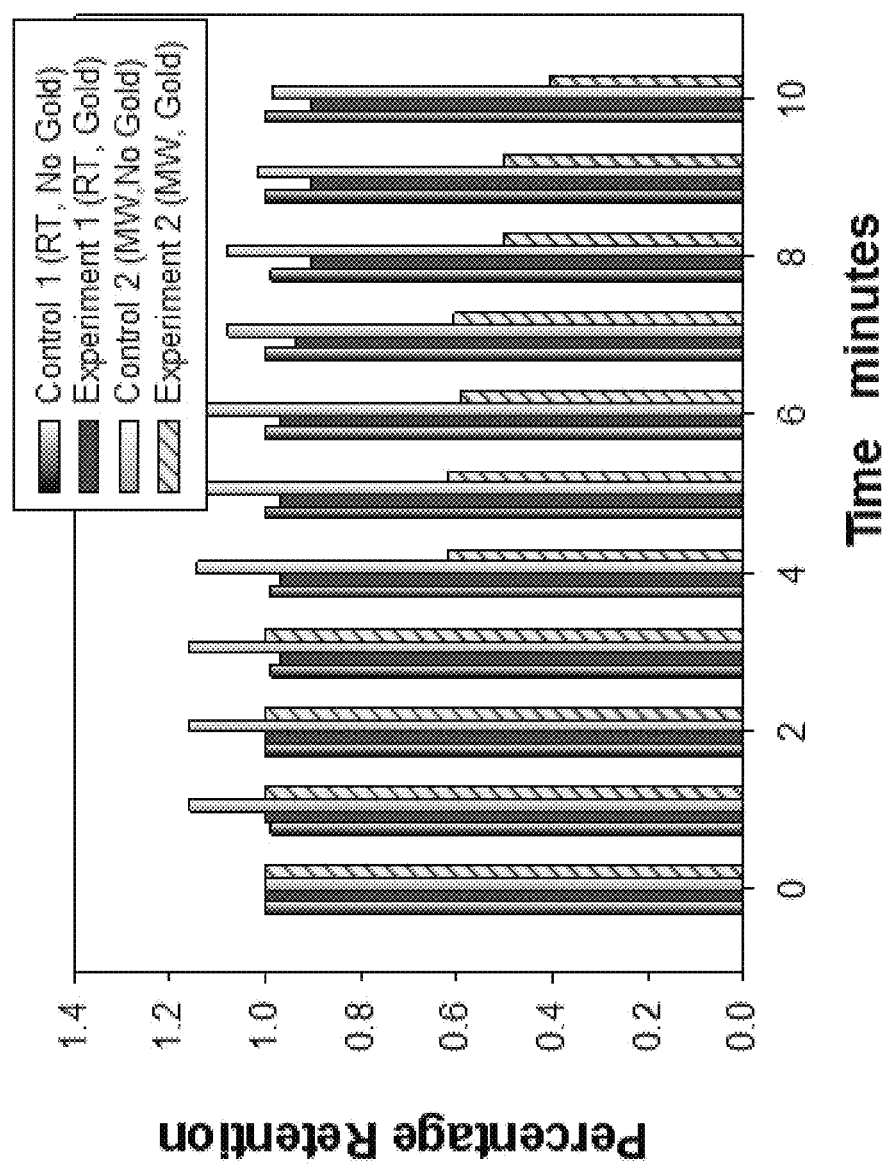
FIG. 6 shows the calculated retention rate of uric acid crystals in all experiments.

In order to assess the effect of the use of gold colloids and microwave heating on uric acid crystals quantitatively, the percentage retention value of uric crystals in all experiments were calculated by dividing the number of crystals at any observation time by the initial number of uric acid crystals and shown on a scale 0 to 1 (FIG. 6). The percentage retention value of uric acid crystals without gold colloids at room temperature (Control 1) remained the same for 10 minutes, which indicated that uric acid crystals did not dissolve in synovial fluid. The incubation of uric acid crystals with the addition of gold colloids at room temperature (Experiment 1) showed a 5% decline in the percentage retention value, which implies that gold colloids in solution results in the de-crystallization of uric acid crystals. When uric acid crystals are exposed to microwave heating without gold colloids (Control 2), the percentage retention value is increased by 15% initially and decreased to the initial level thereafter, which can be attributed to the breakage of larger uric acid crystals into smaller ones (data not shown) and to the partial de-crystallization processes. When uric acid crystals are exposed to microwave heating after the addition of gold colloids (Experiment 2), the percentage retention value is decreased by 40% after 4 minutes and 60% after 10 minutes of microwave heating. The average number and size of uric acid crystals at the end of Experiment 2 was 30±5 and 19±10 micrometers, respectively.

Addressing the mechanism behind de-crystallization using microwave heating with gold colloids, the collision events between the gold colloids present in solution with the uric acid crystals on the glass surface are increased due to an increase in kinetic energy of gold colloids when exposed to microwave heating. By comparison, the collision events between gold colloids and uric acid crystals at room temperature are significantly less due the slow diffusion rates of gold colloids in solution as compared to those exposed to microwave heating. In addition, the number of gold colloids (~1012 particles/mL, typical of chemically synthesized gold colloids) is significantly larger than the number of uric acid crystals (ca. 70 in this study), which results in greater collisions that breakdown and ultimately reduces the size of the uric acid crystals. In these experiments the temperature of the synovial fluid was 24° C. and the temperature change during the exposure to microwave heating in this rapid communication was not measured, but the inventors have previously observed the temperature of the synovial fluid does not exceed 30° C. after 1 minute of microwave heating at power level 1 (i.e., duty cycle of 3 sec).

Figure 7:
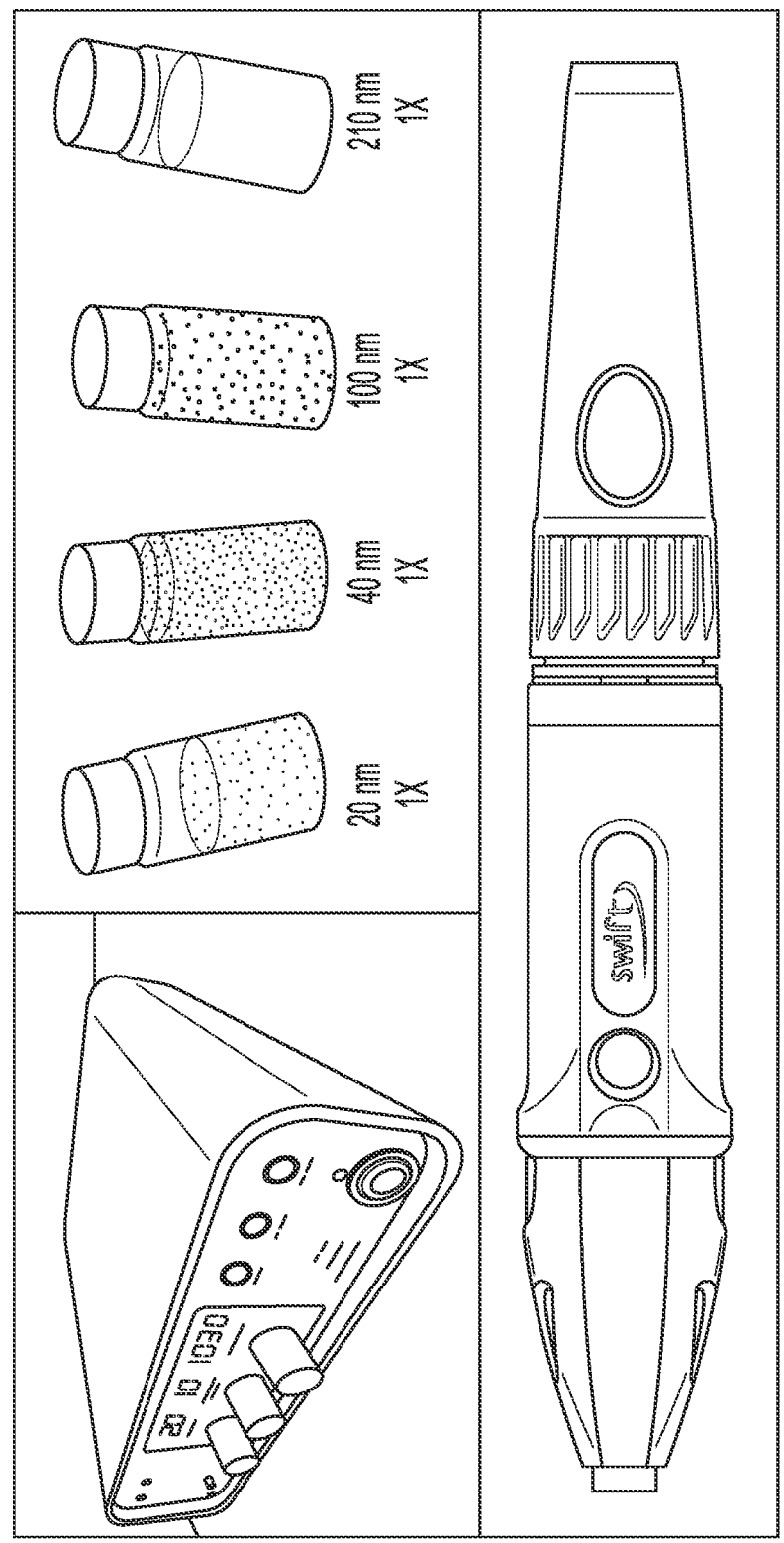
FIG. 7 shows an 8 GHz microwave system and microwave applicator which may be used according to an embodiment of the invention, together with 4 different preparations of 1× concentration gold colloid particles (from left to right, 10 nm, 40 nm, 100 nm and 200 nm).

FIG. 7 shows an 8 GHz microwave system and microwave applicator that may be used according to an embodiment of the invention. The microwave applicator can be prepared by those of ordinary skill in the art, to provide the desired level of microwave energy. The image is provided is an example only and is not to limit the scope of the present invention. The sizes and concentrations of the metal nanoparticles can be varied as well as the microwave energy and time of application. Different variations of the present invention may be used based on the in vivo applications. Many different metal nanoparticles and metal colloids may be used.

The present invention is not restricted to the examples as provided herein.

The invention claimed is:

1. A non-invasive method for the de-crystallization of uric acid crystals into dissolved uric acid, comprising:
   administering, to a mammalian joint where said uric acid crystals are present, a solution containing gold meta colloids having an average diameter of 20 nm to 2000 nm at a concentration of 500 particles/ml to 5,000 particles/ml, and
   applying microwave radiation to said mammalian joint with a non-invasive external microwave applicator for a period of 4 to 20 minutes to result in dissolution of uric acid crystals into uric acid solution, wherein the application of the microwave radiation increases the kinetic energy of the gold metal colloids within solution, precipitating collisions between the gold metal colloids and the uric acid crystals and the dissolution of the uric acid crystals into the uric acid solution.

2. A method according to claim 1, wherein said metal colloids have an average diameter of 40 nm to 100 nm.

3. A method according to claim 1, wherein said metal colloids are present in said solution at a concentration of 750 particles/ml to 2,000 particles/ml.

4. A method according to claim 1, wherein said microwave radiation is applied to said location for a period of 4 to 10 minutes.

5. A method according to claim 1, wherein said mammalian joint is arthritic.

* * * * *